United States Patent [19]
Tittmann et al.

[11] 4,307,614
[45] Dec. 29, 1981

[54] METHOD AND APPARATUS FOR CHARACTERIZING SURFACE FLAWS UTILIZING ULTRASONIC SURFACE WAVES

[75] Inventors: Bernhard R. M. Tittmann, Thousand Oaks, Calif.; Gerard J. Quentin, Paris, France; Frederic S. Cohen Tenoudji, Neuilly sur Seine, France; Alain R. Jungman, Paris, France; Etienne M. M. de Crespin de Billy, Paris, France

[73] Assignee: Rockwell International Corporation, El Segundo, Calif.

[21] Appl. No.: 47,195

[22] Filed: Jun. 11, 1979

[30] Foreign Application Priority Data

Jun. 21, 1978 [FR] France .................. 78 18559

[51] Int. Cl.³ .......................... G01N 29/04
[52] U.S. Cl. .................................. 73/629
[58] Field of Search .................. 73/629, 620, 624, 627, 73/628, 609, 610, 615

[56] References Cited

U.S. PATENT DOCUMENTS

| | | | |
|---|---|---|---|
| 3,512,400 | 5/1970 | Lynnworth | 73/629 |
| 4,052,889 | 10/1977 | Mucciardi et al. | 73/620 |
| 4,058,002 | 11/1977 | Moran | 73/629 |
| 4,121,467 | 10/1978 | Gerhart | 73/629 |

FOREIGN PATENT DOCUMENTS 780752  8/1957  United Kingdom .................. 73/629

OTHER PUBLICATIONS

Krautkramer et al., *Ultrasonic Testing of Materials*, pp. 42, 43, 332–335, 1977.

*Primary Examiner*—Stephen A. Kreitman
*Attorney, Agent, or Firm*—H. Fredrick Hamann; Craig O. Malin; John J. Deinken

[57] ABSTRACT

Disclosed is a method for determining the length of a surface flaw in an object, including the steps of generating a directional beam of ultrasonic waves on the surface of the object toward the flaw and at an angle $\theta$ with respect to the normal to the direction of the flaw, measuring the intensity of the waves reflected from the flaw, at an angle $\theta'$ with respect to the normal, as a function of frequency, and calculating the length 1 of the flaw according to the formula $1 = n\, V_R/[f_n(\sin\theta + \sin\theta')]$ where n is a integral number defining the order of the frequency minimu, $V_R$ is the speed of the surface waves in the object, and $f_n$ is the frequency at which a minimum of intensity occurs. Also disclosed is an apparatus for evaluating a surfacae flaw in an object including a transducer for inducing ultrasonic surface waves, a signal generator driving the transducer, a deteactor for responding to reflected waves, an amplifier to boost the detector response, a spectrum analyzer to measure the intensity of the reflected waves as a function of frequency, and a gating device to apply the output of the amplifier to the spectrum analyzer durng a predetermined time interval.

10 Claims, 7 Drawing Figures

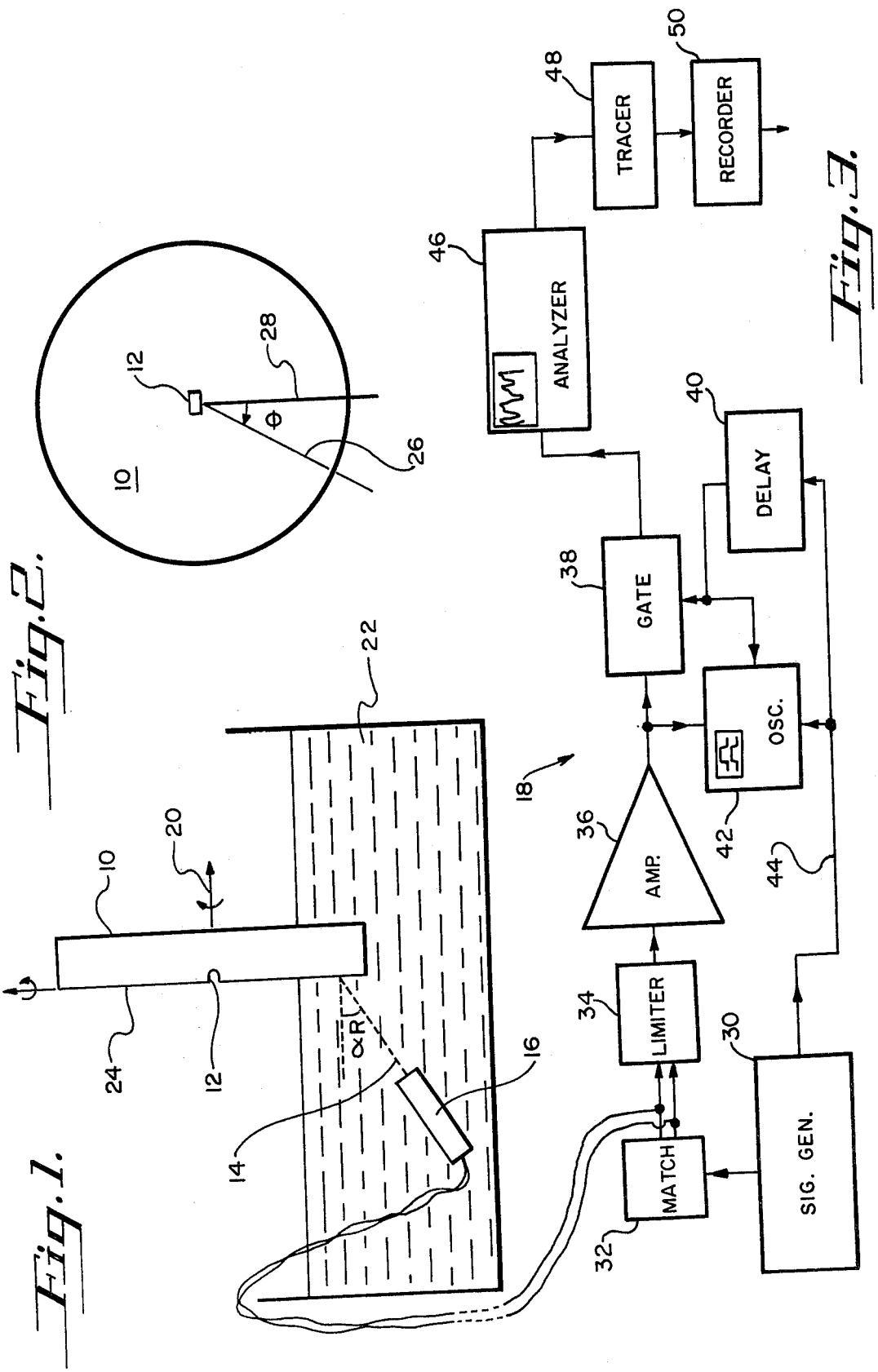

METHOD AND APPARATUS FOR CHARACTERIZING SURFACE FLAWS UTILIZING ULTRASONIC SURFACE WAVES

BACKGROUND OF THE INVENTION

This invention is related to the field of nondestructive testing, and more particularly, to nondestructive testing utilizing ultrasonic waves.

A number of ultrasonic testing methods have been developed using ultrasonic waves. Bulk wave modes, for example, which propagate through a solid material, have been employed to detect flaws in parts and to measure the thicknesses of such parts. Although bulk ultrasonic waves may be utilized for the qualitative detection of flaws, bulk wave testing has not been sufficiently precise to quantify flaws as to their length, depth, orientation, etc. Bulk wave modes have also been suggested for use in determining the condition of the surface of a material. In this application, a test object is irradiated with ultrasound while immersed in water, the spectroscopy of the reflected ultrasonic waves providing an indication of perodic or quasi-periodic roughness on the surface (see, e.g., F. Cohen-tenoudji et al., Caractérisation de surfaces rugueuses périodiques ou quasi-périodiques par spectroscopie ultrasonore, communication présentée a la huitiéme conférence mondiale sur less essais non destructifs, Cannes, Frances, Septembre, 1976; A. Jungman et al., Diffraction Experiments in Ultrasonic Spectroscopy; preliminary results on the characterization of periodic or quasi-periodic surfaces; Conference Proceedings, Ultrasonics International, pp. 385–396, Brighton, England 1977, published by IPC Business Press Limited).

The ultrasonic test methods which have been heretofore known and developed, however, are not sufficiently precise to accurately measure the dimensions of surface flaws, particularly the length of such flaws. The length of a flaw is a useful quantity to be determined, since it would be useful for considerable applications in materials testing where it can be related to the remaining useful life of a part containing the flaw. Thus, it would be advantageous to provide a nondestructive test which measures the length of a flaw and permits the flaw length to be monitored as the flaw dimensions change during the life of the part.

SUMMARY OF THE INVENTION

It is a general object of this invention to provide a new and improved apparatus and method for characterizing surface flaws in an object.

A method for evaluating a surface flaw in an object, according to this invention, includes the steps of:

(a) generating a directional beam of ultrasonic waves on the surface of the object toward the flaw and at an angle $\theta$ with respect to a normal to the direction of the flaw;

(b) measuring the intensity of the waves reflected from the flaw, at an angle $\theta'$ with respect to the normal, as a function of frequency; and (c) characterizing the flaw according to the frequencies for which intensity minima were measured to step (b).

In a preferred embodiment, step (c) consists of calculating the length $l$ of the flaw according to the formula $$l = nV_R/[f_n(\sin\theta + \sin\theta')],$$

where:

$n$ = an integral number defining the order of the frequency minimum;
$V_R$ = the speed of the surface waves in the object; and
$f_n$ = the frequency at which a minimum intensity occurs.

An enhanced estimate may be obtained by:

(d) repeating step (c) for a plurality of frequency minima $f_n$; and (e) averaging the values obtained for $l$.

A further enhanced estimate may be obtained by:

(f) repeating steps (a)–(e) for a plurality of incident angles $\theta$; and (g) averaging the averaged values of $l$ obtained in step (f).

Examples of the more important features of this invention have been broadly outlined above in order that the detailed description which follows may be better understood, and so that the contributions which this invention provides to the art may be better appreciated. There are, of course, additional features of the invention which will be described below and which are included within the subject matter of the claims appended hereto.

BRIEF DESCRIPTION OF THE DRAWINGS

Additional features, objects, and advantages of the present invention will become apparent after referring to the detailed description of the preferred embodiments below in connection with the accompanying drawings, wherein like reference numerals refer to like elements throughout all the figures. In the drawings:

FIG. 1 is a cross-sectional view illustrating a typical experimental transducer and test object arrangement for practicing the present invention;

FIG. 2 is a side elevation of an object containing a flaw, further illustrating the test arrangement shown in FIG. 1;

FIG. 3 is a schematic illustration showing an electronic apparatus arranged according to this invention to be used in connection with the experimental arrangement of FIG. 1;

DESCRIPTION OF THE PREFERRED EMBODIMENT

Figure 4:
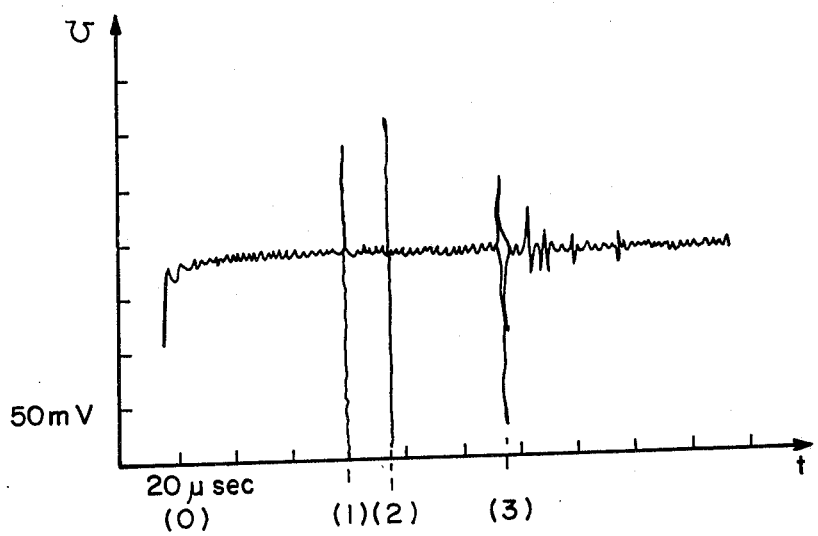
FIGS. 4 and 5 are reproductions of oscilloscope traces recorded during an experimental test of the present invention using the apparatus illustrated in FIGS. 1–3.

Now referring to the drawings, and first to FIGS. 1 and 3, a typical test arrangement for practicing the present invention is illustrated. A test object 10, containing a surface flaw 12, is irradiated with a directional beam of ultrasonic waves 14 by a transducer 16. Waves reflected from the flaw are detected by the transducer and the resulting signal is analyzed by sensing electronics 18 to provide data from which the length of the flaw 12 can be calculated. In the course of developing the present invention, it has been found that significant improvements in the information obtained by the application of surface ultrasonic waves to a surface flaw can be attained over previously known ultrasonic test methods. Ultrasonic surface waves may be considered to travel along a principal direction as a plane wave, in which case the wave may be treated as a directional beam of ultrasonic energy. If the flaw of interest is in the form of a surface flaw whose depth in the object is sufficiently beyond the relatively shallow propagating region of a surface wave, and if the edges of the flaw are approximately straight (i.e., the radius of curvature is large compared to the ultrasonic wavelength), the length of the flaw can be computed, according to this invention, by measuring the amplitude of the wave energy reflected from the crack as a function of the frequency.

According to an outstanding feature of this invention, the length l of the crack is determined according to the formula $$l = n\, V_R/f_n (\sin\theta + \sin\theta') \quad (1)$$

where:

$n$ = an integral number defining the order of the frequency minimum;
$V_R$ = the speed of the surface waves in the object;
$f_n$ = the frequency at which a minimum of intensity occurs;
$\theta$ = the angle between the incident beam and the normal to the crack; and
$\theta'$ = the angle between the reflected beam and the normal.

It can be shown from equation (1) that the order n of a particular minima which is observed is:

$$n = f_n/\Delta f_n \quad (2)$$

where $\Delta f_n$ is the difference in frequency between two consecutive minima. If a single minimum is detected, n=1 where the pass band of the system is at least twice as large as the low frequency cutoff of the system.

Thus, values for $f_n$ (i.e., $f_1, f_2, f_3 \ldots$) may be determined experimentally and values for n corresponding to the $f_n$ values (i.e., n=1, 2, 3 ...) may be calculated from equation (2). By then substituting the values for n and $f_n$ into equation (1), together with known values of $V_R$, $\theta$, and $\theta'$, the length of a surface flaw may be calculated.

A theoretical model which supports this technique may be derived based on the assumptions that (a) the radius of curvature of the boundary of the crack is small compared to the wavelength of the surface waves, and (b) that the form of the bottom of the crack does not have an appreciable effect, since the surface waves do not penetrate to the bottom of the crack.

Because of assumption (a), the reflected surface wave may be expressed as the Fourier transform of the complex amplitude of the incident surface wave through an opening of the length l, assuming that ultrasonic surface waves obey laws similar to the laws of optical diffraction. If the reflected intensity is designated as I ($\theta$, f) (i.e., I is variable as a function of the incident angle $\theta$ and the frequency (f), the intensity can thus be written, making assumption (b), as:

$$I(\theta, f) = I(0, f)\, \sin^2\psi/\psi^2 \quad (3)$$

where $$\psi = \pi l\, f \sin\theta / V_R. \quad (4)$$

Equation (3) may be transposed to obtain the intensity ratio $$\frac{I(\theta, f)}{I(0, f)} = \frac{\sin^2\psi}{\psi^2} \quad (5)$$

As can be observed from the form of equation (5), minima of intensity will occur for values of $\psi = 0$ (i.e., where Sin $\theta = 0$), corresponding to particular frequencies of the ultrasonic spectrum. These frequency minima, which may be designated $f_n$, can be shown to be related to the length l of the crack by:

$$l = n\, V_R/2f_n \sin\theta. \quad (6)$$

It may be noted that equation (6) is equivalent to equation (1) where $\theta = \theta'$.

Now referring to FIG. 1, an apparatus adapted to practice the present invention is illustrated. In FIG. 1, a test object 10, which contains a surface crack 12, is rotatably mounted about axis 20 which passes through the center of the crack 12. A directional beam of ultrasonic waves 14 is produced in a reservoir of water 22 by a transducer 16. The transducer is positioned with respect to the surface 24 of the object 10 so that the directional beam 14 impinges on the surface at the critical Rayleigh angle $\alpha_R$. In this manner, the directional beam 14 is converted to a surface wave which propagates along the surface 24. Although the object 10 is immersed in the reservoir 22 so that the juncture of the beam 14 with the object 10 is under water, the crack 12 is kept out of the water to avoid excessive attenuation of the sound waves reflected from the crack.

As best illustrated in FIG. 2, the rotational mounting for the object 10 affords adjustment of the angle $\theta$ which the incident surface wave 26 makes with respect to the normal 28 to the direction of the crack 12. Thus, by rotating the object 10, measurements may be taken for various angles of incident ultrasonic waves on the crack 12.

Now referring to FIG. 1, in conjunction with FIG. 3, the directional beam 14 is produced by a signal generator 30 which applies periodic impulses through an impedance matcher 32 to the transducer 16. The rise time of the impulses supplied by the generator 30 is made sufficiently short to excite the transducer 16 over a usefully wide band of frequencies.

In the embodiment illustrated, the transducer 16 also functions to detect the waves which are reflected from the crack 12. The resulting signal from the transducer passes through a limiter 34, which filters out the exciting signal from the generator 30, and thence to an amplifier 36, which is a wideband amplifier having a large dynamic range.

The output from the amplifier 36 is applied to an analog gate 38, which passes only that portion of the signal occurring in a set time interval. A time delay generator 40 controls the time at which the time interval imposed by the gate 38 begins, relative to the time a pulse is generated by the generator 30.

A dual trace oscilloscope 42 receives inputs from both the time delay generator 40 and the output of the amplifier 36. The oscilloscope sweep is triggered by a signal 44 from the signal generator 30, as is the time delay generator. Using the oscilloscope 42, an operator may thus adjust the time delay as well as the width of the interval for which the output of amplifier 36 is permitted to pass through gate 38. In this manner, the generator can arrange a pass band for that portion of the output signal which is attributable to the reflected wave from the crack 12. Thus isolated, the reflected wave signal is applied to a spectrum analyzer 46. The output of the spectrum analyzer is then processed to provide an indication of the amplitude present as a function of frequency in the processed signal. In the embodiment illustrated in FIGS. 1 and 3, this processing is accomplished by applying the output of the spectrum analyzer 46 to a curve tracer 48. The curve tracer provides a voltage output, the variation of which over time represents the spectral intensity of the reflected wave.

The output of the curve tracer is then further analyzed. A recorder 50, for example, can be connected to the output of the curve tracer to provide a graphical representation of intensity versus frequency data for the reflected wave, or the signal may be applied to an analog to digital converter and processed by digital methods.

Although the analog gate 38 provides a simple and convenient means for selectively detecting that portion of the signal representing a reflection from the crack 12, those skilled in the art will appreciate that other ways could be utilized, such as, for example, digitizing the signal output from the amplifier 36 and applying numerical methods to the digitized signal.

In practicing the method of this invention with the apparatus illustrated, an ultrasonic surface wave is produced by the transducer 16 in response to an impulse from the generator 30. At least one reflected wave is then detected in a chosen delay interval by the transducer 16 and the sensing electronics 18. It is advantageous in this procedure to produce a repeating series of surface waves and a corresponding series of detections of a reflected wave, for a constant $\theta$ and a constant delay interval.

The procedure may also advantageously be repeated several times for varying values of the angle $\theta$. To determine the general direction of the crack, the direction of the incident beam for which an overall maximum of intensity occurs is measured, that direction establishing the normal to the crack direction. Once this direction is determined, and angle $\theta$ for each test run may be set.

Preferably the test is conducted with the incident beam and the detected waves covering the same bandwidth of frequencies. The ultrasonic beam generated should have a half bandwidth of at least 30% of the value of the median frequency of the band, and preferably the half bandwidth should be near 60% of the median frequency.

From the data which is obtained relating frequency to intensity, frequency minima can be determined and the appropriate values substituted in equation (1) to obtain an estimate of the length l of the crack.

To obtain a precise measurement of the length, it is desirable to normalize the spectrum of intensity as a function of frequency, by relating the intensity for a given angle and frequency to the intensity for that frequency at an angle $\theta=0$ (i.e., for an incident beam perpendicular to the length of the crack), as indicated in equation (3).

A normalized spectrum may also be obtained by determining the spectrum of the frequencies transmitted into the object and the response curve of the detection system. An approximate normalization then can be computed by correlating this spectrum to the response curve.

Although the length of a crack may be determined by this method using a single minimum of the reflected frequency spectrum, an estimate of increased accuracy may be obtained by calculating values of the length from the data for several minima and averaging. Further accuracy may be achieved by calculating the length from the data for incident beams at several angles of incidence and averaging.

In a particular experiment designed to test the method and apparatus of the present invention, a Duralumin disc 120 mm in diameter was struck in the center by a flat punch, producing a crack having a semicircular cross section at its lower edge. An ultrasonic transducer with a wideband absorption (type F 10-D7 No. 484/EL, Compagnie Générale de Radiologie) was excited by an impulse having a rise time of 50 nanoseconds.

The sensing electronics included a preamplifier having a wide band (20 MHz) and a large dynamic range (40 dB). With this arrangement, and without the application of an analog gate and a time delay generator to impose a pass band, an oscilloscope connected as shown in FIG. 3 exhibited the trace illustrated in FIG. 4. Indicated at (0) is the end of the transducer-exciting pulse, while the spike at (1) is due to a reflection at the water-/air interface, the spike at (2) represents the reflection from the crack, and the spike at (3) results from a reflection at the edge of the test disc.

Figure 5:
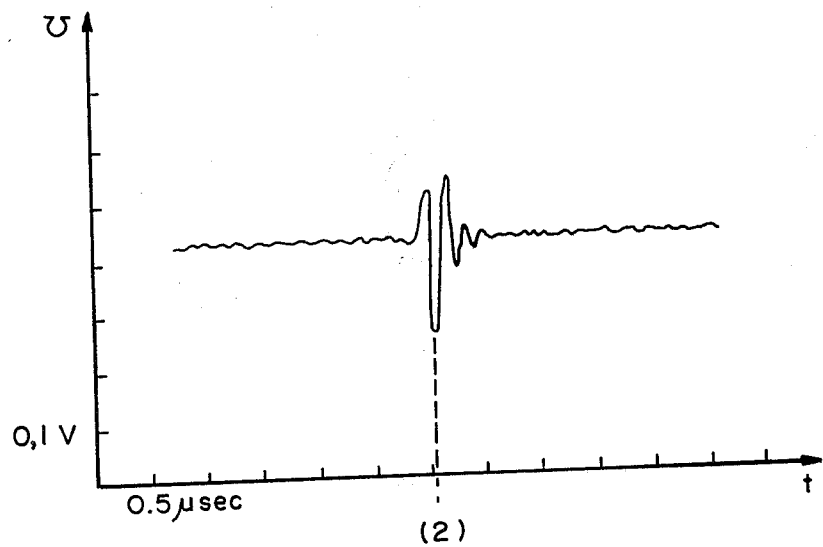
Figure 6:
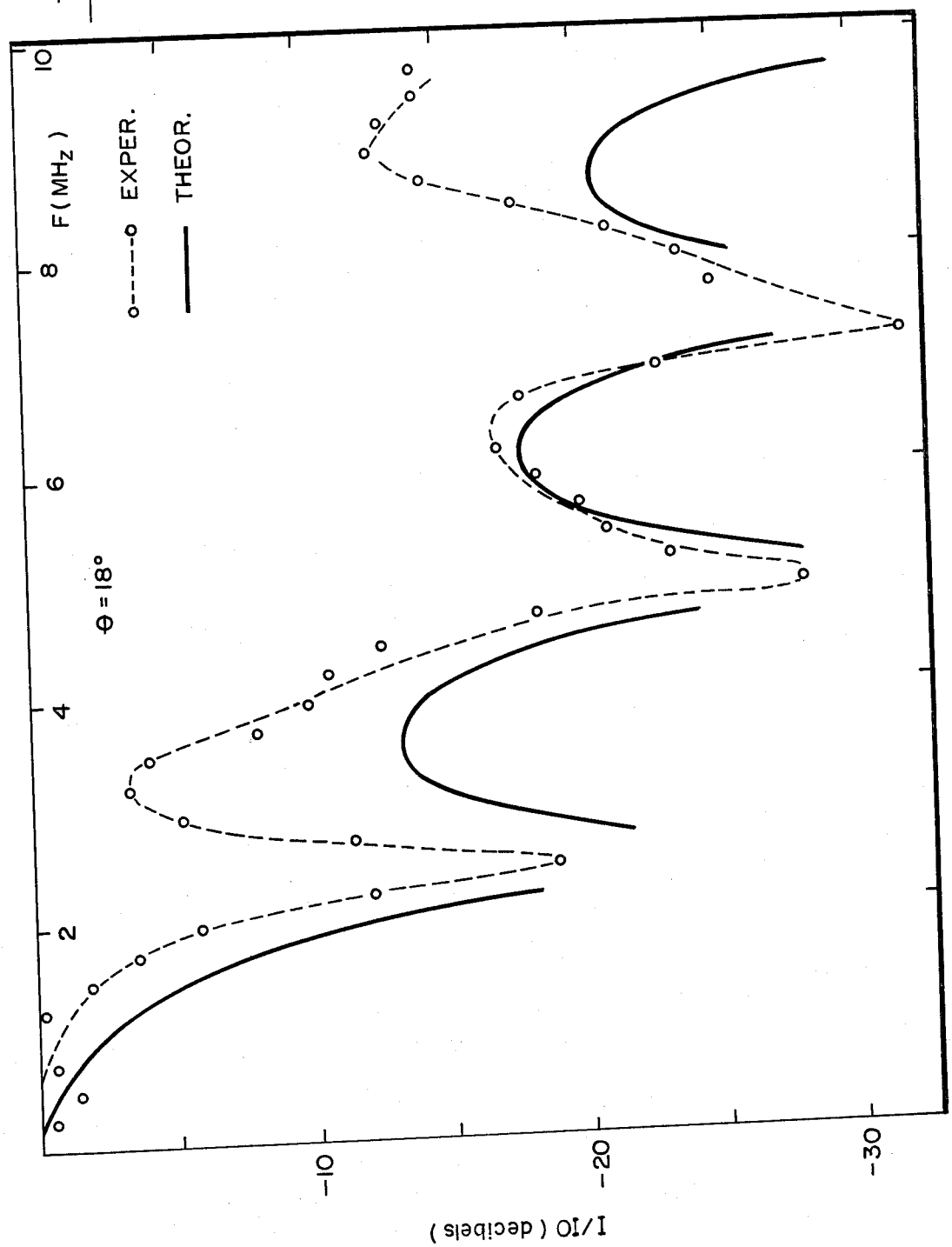
FIGS. 6 and 7 provide graphical depictions of both experimental and theoretical relationships obtained between relative intensity and frequency using the method and apparatus of the present invention.
Figure 7:
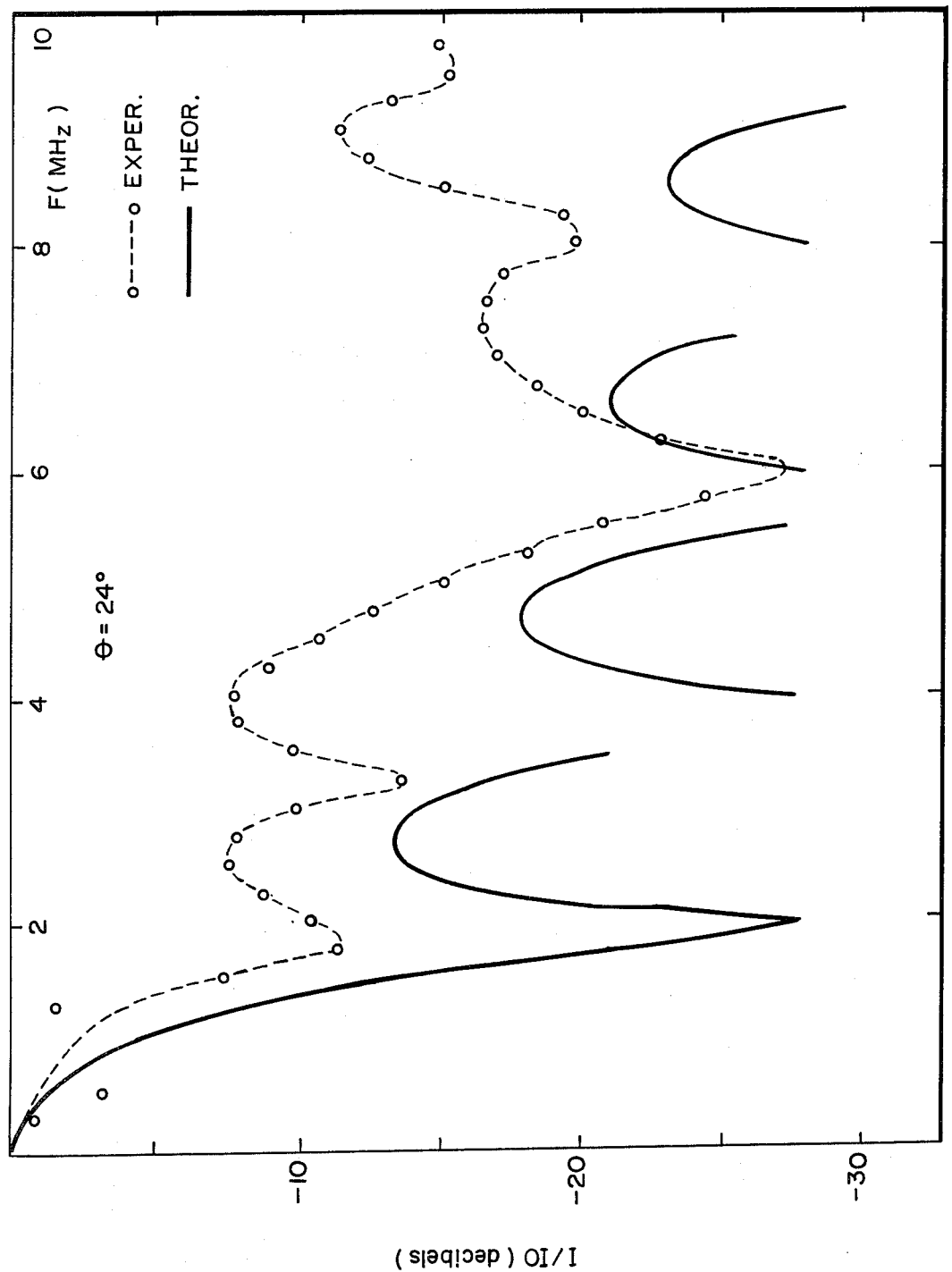

By adjusting the analog gate and the time delay generator, the sensing electronics may be focussed, via a pass band, on the reflection at (2) from the crack. FIG. 5 illustrates the resulting oscilloscope trace, with an expanded time base. In this experiment, the signal shown in FIG. 5 was applied to a spectrum analyzer (Hewlett-Packard, sections 8552B and 8553B with plug-ins 141T). The experiment was conducted at several angles of incidence and data was gathered for an angle $\theta$ of 0°, 18°, and 24°. The results of the experiment are plotted with dashed lines for normalized intensities in FIGS. 6 and 7 for a $\theta$ of 18° and 24°, respectively. Also plotted in those figures, with solid lines, are theoretical response curves obtained by substituting values in the theoretical equation (5). A comparison of the curves shows that the theoretical model provides a good estimate of experimental results. In FIG. 6, minima of intensity are found at frequencies $f_1=2.5$ MHz, $f_2=5$ MHz, and $f_3=7.5$ MHz. Since the Rayleigh speed $V_R$ in Duralumin is 2923 m/s, the length of the crack is calculated to be $l=1.891\pm0.020$ mm. Visual measurement of the length of the crack under magnification led to an estimate of $l=1.875\pm0.025$ mm. Thus, the correlation between the experimental and theoretical curves in the figure is confirmed by the actual length of the crack. Some of the deviation between the theoretical and experimental values may be explained by the fact that the crack was not perfectly straight and thus the actual length and apparent length of the crack were not the same.

Thus, the experimental results confirm that the ultrasonic surface wave reflected from a surface flaw will exhibit a characteristic spectrum which is related to the size and shape of the flaw, constituting a "signature" of the flaw which may be used to characterize it.

Although a typical embodiment of the present invention has been illustrated and discussed above, numerous modifications and alternative embodiments of the method of this invention will be apparent to those skilled in the art in view of this description. The experimental arrangement utilizing a water to sample interface, for example, is only one convenient technique for exciting surface waves in a material. Other techniques may be equally useful in practicing this invention. A transducer, for example, may be provided with a plastic tip and coupled to the material by a suitable glue or grease. Accordingly, this description is to be construed as illustrative only, being provided for the purpose of teaching those skilled in the art the manner of performing the method of the invention. Furthermore, it is to be understood that the form of the invention shown and described is to be considered the presently preferred embodiment. Various changes may be made in the configurations, sizes, and arrangements of the parts of the invention, as will be recognized by those skilled in the art, without departing from the scope of the invention. Equivalent elements, for example, might be substituted for those illustrated and described herein, parts or connections might be reversed or otherwise interchanged, and certain features of the invention might be used independently of the use of other features, all as will be apparent to one skilled in the art after receiving the teaching which will be obtained by reading the foregoing description of the invention.

What is claimed is:

1. A method of determining the length of a surface flaw in an object, comprising the steps of:
   (a) generating a directional beam of ultrasonic waves on the surface of the object toward the flaw and at an angle $\theta$ with respect to a normal to the direction of the flaw;
   (b) measuring the intensity of the waves reflected from the flaw, at an angle $\theta$ with respect to the normal, as a function of frequency; and
   (c) characterizing the flaw according to the frequencies for which intensity minima were measured in step (b).

2. The method of claim 1, wherein step (c) of characterizing the flaw comprises:
   calculating the length l of the flaw according to the formula $$l = n\ V_R/[f_n(\operatorname{Sin}\theta + \operatorname{Sin}\theta')]$$

where:
   n = an integral number defining the order of the frequency minimum;
   $V_R$ = the speed of the surface waves in the object; and
   $f_n$ = the frequency at which a minimum of intensity occurs.

3. The method of claim 2, further comprising the steps of:
   (d) repeating step (c) for a plurality of frequency minima $f_n$; and
   (e) averaging the values obtained for 1.

4. The method of claim 3, further comprising the steps of:
   (f) repeating steps (a)–(e) for a plurality of incident angles $\theta$; and
   (g) averaging the averaged values of l obtained in step (f).

5. The method of claim 4, further comprising the step of:
   (h) determining the incident beam direction for which a maximum reflected intensity occurs, the direction of maximum intensity corresponding to an angle $\theta$ of 0°.

6. The method of claim 1, wherein step (b) further comprises measuring the intensity of the waves reflected from the flaw in a selected time interval after the directional beam is generated.

7. The method of claim 6, wherein step (b) further comprises applying a Fourier transform to the time domain reflected waves to determine the intensity of the waves as a function of frequency.

8. The method of claim 1, wherein step (a) further comprises generating a broadband directional beam of ultrasonic waves.

9. A method of determining the length of a surface flaw in an object, comprising the steps of:
   (a) generating a broadband directional beam of ultrasonic waves on the surface of the object toward the flaw and at an angle $\theta$ with respect to a normal to the direction of the flaw;
   (b) measuring the intensity of the waves reflected from the flaw, at an angle $\theta'$ with respect to the normal, as a function of frequency; and
   (c) calculating the length l of the flaw according to the formula $$l = n\ V_R/[f_n(\operatorname{Sin}\theta + \operatorname{Sin}\theta')]$$

where:
   n = an integral number defining the order of the frequency minimum;
   $V_R$ = the speed of the surface waves in the object; and
   $f_n$ = a frequency at which a minimum of intensity occurs.

10. A method of determining the length of a surface flaw in an object, comprising the steps of:
    (a) generating a broadband directional beam of ultrasonic waves on the surface of the object toward the flaw and at an angle $\theta$ with respect to a normal to the direction of the flaw;
    (b) measuring the intensity of the waves reflected from the flaw, at an angle $\theta$ with respect to the normal, as a function of frequency;
    (c) calculating the length l of the flaw according to the formula $$l = n\ V_R/[f_n(\operatorname{Sin}\theta + \operatorname{Sin}\theta')]$$

where:
    n = an integral number defining the order of the frequency minimum;
    $V_R$ = the speed of the surface waves in the object; and
    $f_n$ = a frequency at which a minimum of intensity occurs;
    (d) repeating step (c) for a plurality of frequency minima $f_n$;
    (e) repeating steps (a)–(d) for a plurality of incident angles $\theta$.

* * * * *